(12) United States Patent
Hsieh et al.

(10) Patent No.: US 6,415,013 B1
(45) Date of Patent: Jul. 2, 2002

(54) BACKPROJECTION METHODS AND APPARATUS FOR COMPUTED TOMOGRAPHY IMAGING SYSTEMS

(75) Inventors: Jiang Hsieh, Brookfield, WI (US); Stephen W. Metz, Paris (FR); Sharon X. Wang, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/751,225

(22) Filed: Dec. 28, 2000

(51) Int. Cl.$^7$ .................................................. A61B 6/03
(52) U.S. Cl. ............................. 378/19; 378/4; 378/901; 382/131
(58) Field of Search ................................ 378/4, 15, 19, 378/901; 382/131

(56) References Cited

U.S. PATENT DOCUMENTS

| | | | | |
|---|---|---|---|---|
| 4,894,775 A | * | 1/1990 | Kritchman et al. | 378/4 |
| 5,473,654 A | * | 12/1995 | Kotian et al. | 378/4 |
| 5,625,660 A | | 4/1997 | Tuy | |
| 5,708,691 A | | 1/1998 | Zmora | |
| 5,825,842 A | | 10/1998 | Taguchi | |
| 5,907,593 A | * | 5/1999 | Hsieh et al. | 378/4 |
| 5,909,476 A | * | 6/1999 | Cheng et al. | 378/4 |
| 5,960,056 A | * | 9/1999 | Lai | 378/4 |
| 6,072,851 A | | 6/2000 | Sivers | |
| 6,256,366 B1 | * | 7/2001 | Lai | 378/4 |
| 6,285,732 B1 | | 9/2001 | Hsieh | |
| 6,307,908 B1 | * | 10/2001 | Hu | 378/15 |
| 6,324,241 B1 | * | 11/2001 | Besson | 378/4 |
| 6,327,325 B1 | * | 12/2001 | Hsieh | 378/4 |

* cited by examiner

Primary Examiner—Drew A. Dunn
(74) Attorney, Agent, or Firm—Carl B. Horton, Esq.; Armstrong Teasdale LLP

(57) ABSTRACT

There is therefore provided, in one embodiment of the present invention, a method for reconstructing a volume image of an object. The method includes steps of scanning an object with a multislice computed tomographic (CT) imaging system having a multislice detector array to acquire projection data of a volume of the object; filtering the acquired projection data; and backprojecting the filtered projection data to reconstruct voxels of the volume image. The multislice detector array has a plurality of rows and columns of detector elements and the backprojecting includes interpolating the filtered projection data across both rows and columns of the multislice detector array.

16 Claims, 5 Drawing Sheets

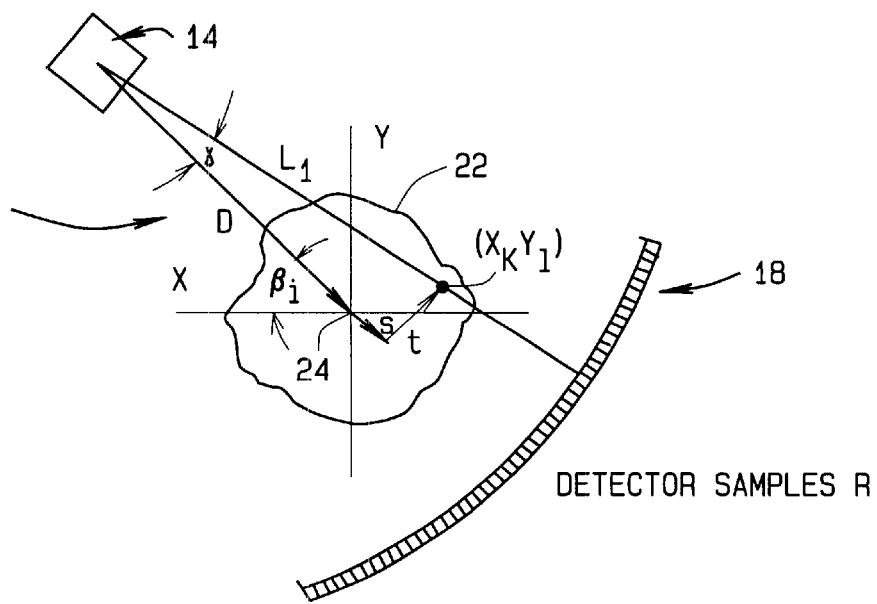
Prior Art  FIG. 3
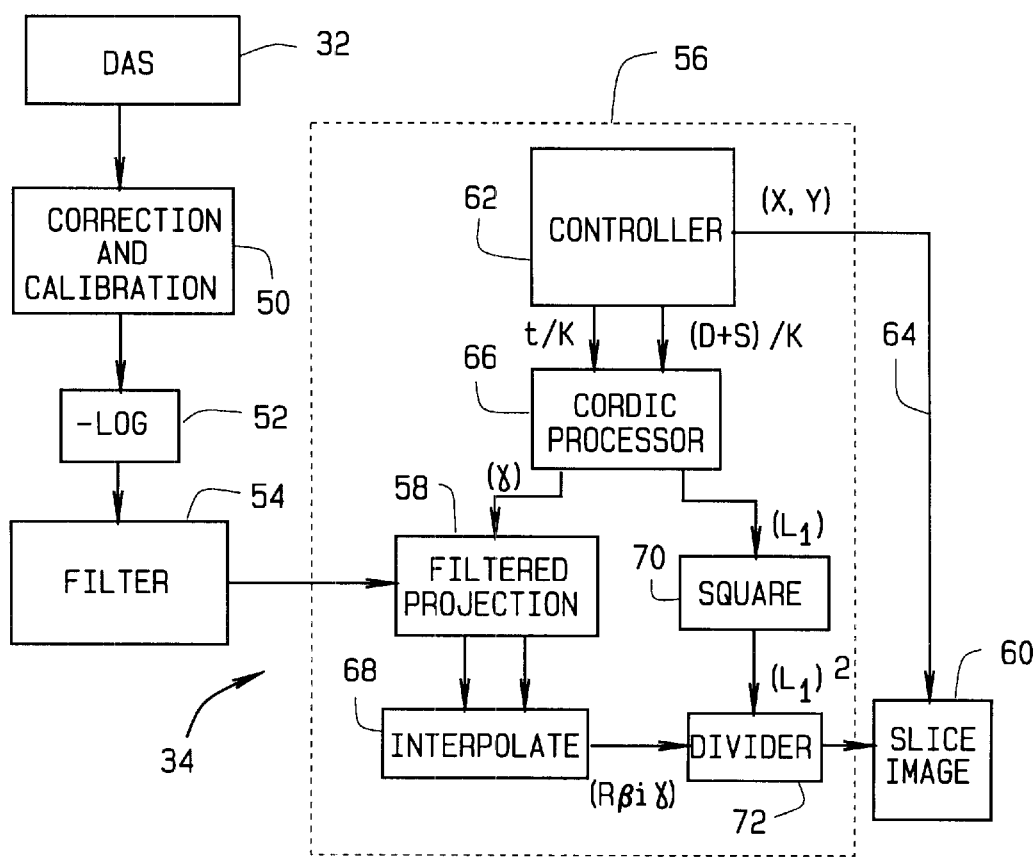
FIG. 4  Prior Art

BACKPROJECTION METHODS AND APPARATUS FOR COMPUTED TOMOGRAPHY IMAGING SYSTEMS

BACKGROUND OF THE INVENTION

This invention relates generally to multislice computed tomography (CT) imaging apparatus and methods, and more particularly to methods and apparatus for backprojecting attenuation data acquired during a scan to form an image.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

More specifically, and referring to FIGS. 1 and 2, one known computed tomography (CT) imaging system 10 includes a gantry 12 representative of a "third generation" CT scanner. Gantry 12 has an x-ray source 14 (or more generally, a radiation source 14) that projects a beam of x-rays 16 (or more generally, a beam of radiation) toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multislice configuration. In a multislice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information t o DAS 32, x-ray controller 28 and gantry motor controller 30. In addition, computer 36 operates a table motor controller 44 which control s a motorized table 46 to position patient 22 in gantry 12. Particularly, table 46 moves portions of patient 22 through gantry opening 48.

In embodiments of imaging system 10 that employ detector arrays 18 having only a single row, only fan-beam backprojection is utilized for reconstruction of images.

Referring to the planar geometry of FIG. 3, the basic geometry for backprojecting a set of corrected and filtered detector samples $R(\beta_i,\gamma_j)$ for a particular pixel is shown. The pixel is located at coordinates $(x_k,Y_l)$ and the gantry angle is $\beta$ (for view number i). D is the distance from x-ray source 14 to isocenter 24, and $\gamma$ is the angle between a ray passing through isocenter 24 and a ray passing through the pixel.

Fan-beam backprojection of the detect or samples $R(\beta_i,\gamma_j)$ in one known imaging system is accomplished in three steps for each pixel. First, the value of the filtered detector pixel must be calculated for the ray passing through the pixel. The angle $\gamma$ is calculated, using interpolation between filtered detector samples that lie to each side of the angle $\gamma$ to yield a precise filtered projection value $R(\beta_i,\gamma)$. Second, the distance $L_1$ between x-ray source 14 and the pixel $(x_k,Y_l)$ is calculated, and finally the value $R(\beta_i, \gamma)/(L_1)^2$ is calculated and added to the pixel value.

To simplify these calculations, an alternative coordinate system defined by s and t is used rather than x and y. The s axis lies a long a line from source 14 to isocenter 24 while the t axis passes through isocenter 24 at a right angle to the s axis. Thus, the s and t coordinates are simply the x and the y coordinates rotated by the gantry angle. Values for s are positive from isocenter 24 towards detector array 18 and negative from isocenter 24 towards source 14. Values for t are positive for positive $\gamma$ and negative for negative $\gamma$.

The value of $\gamma$ using this coordinate system is written:

$$\gamma = \tan^{-1}\left(\frac{t}{D+s}\right).$$

Rarely will $\gamma$ exactly equal one of the discrete $y_j$ values that correspond to one of the detector samples $R(\beta_i,\gamma_j)$. Instead, $\gamma$ will usually lie between two $\gamma_j$ values. In this general case, linear interpolation is used to approximate the actual value of $R(\beta_i,\gamma)$.

Using the Pythagorean theorem, the value of L is written:

$$L=\sqrt{t^2+(D+s)^2}.$$

The values of $\gamma$ and L are calculated directly by a pipeline CORDIC processor of a type described in U.S. Pat. No. 4,896,287 and in J. E. Volder, "The CORDIC Trigometric Computing Technique," *IRE Transactions on Electronic*

Computers, September 1959, pp. 330–334. The CORDIC (COordinate Rotation DIgital Computing) algorithm is an efficient algorithm that computes certain transcendental functions. The algorithm is time-efficient because it replaces multiplication and division operations by shift operations, leaving additions as the only costly computation. The CORDIC processor accepts and inputs two values A and B and makes the following computations:

$$\theta = \tan^{-1}(B/A);$$

and $$r = k\sqrt{A^2 + B^2};$$

where $$k = \prod_{i=0}^{n-2} \sqrt{1 + 2^{-2i}},$$

through a series of vector rotations of angle and scaling steps. By substituting pixel coordinate t for input B and the pixel coordinate D+s for input A, the CORDIC processor computes the values of γ and kL directly. Inputs t and D+s are prescaled by dividing by k in one embodiment so that the desired values of γ and L are directly produced. The constant k is a known constant based on a number of pipeline stages used to implement the CORDIC processor. The filtered projection data value $R(\beta_i, \gamma)$ is then determined using γ, and it is divided by $L^2$ to produce the amount added to the pixel value. Each acquired view during the scan is backprojected in this manner to each pixel in the 2D image being reconstructed.

Referring to FIGS. 1, 2, 3, and 4, during a scan, a series of views ($\beta_i$) of patient 22 is acquired as gantry 12 rotates around an axis that passes through isocenter 24. Each view of scan data is received from DAS 32 and further processed in image reconstructor 34. Details of the additional processing are shown in to FIG. 4. More particularly, each view of scan data is received from DAS 32 and further processed 50 to correct for various well-known errors such as variations in detector and channel gains. The corrected data is log adjusted 52 by taking the negative of its logarithm to provide a projection profile that indicates the amount of attenuating material in patient 22 along the x-ray beam associated with each detector element 20. The projection profile is then filtered 54 by convolving it with a reconstruction filter kernel in preparation for backprojection.

Each filtered projection profile $R(\beta_i, \gamma_j)$ is applied to a backprojector 56 that stores these values in a projection memory 58. Backprojector 56 determines from the filtered projection profile $R(\beta_i, \gamma_j)$ what values must be added to each pixel (x,y) in a slice image 60 being reconstructed in memory. A controller 62 operates backprojector 56 by outputting the coordinates (in this case, the x and y dimensions) of the pixel to be updated at 64 and by outputting corresponding values t/k and (D+s)/k for this pixel into a CORDIC processor 66 that produces an angle γ and distance L of each pixel location from x-ray source 14. The value of γ is used to read two adjacent values from the filtered projection 58. These two values are applied to an interpolator 68 to linearly interpolate between the two values to produce the filtered backprojection value $R(\beta_i, \gamma)$ for a ray through the pixel x,y.

The value of L produced by the CORDIC processor 60 is squared in a multiplier 70 and applied to a divider 72 that divides the filter projection value $R(\beta_i, \gamma)$ by the distance squared of the pixel from x-ray source 14 ($L^2$). Controller 62 repeats this backprojection process for each pixel in slice image 60 to completely backproject the filtered projection data for one view. The next view is then applied to backprojector 56 and the process repeats to update each pixel value in slice image 60 with the contribution from this view. When all views have been acquired and backprojected, slice image 60 accurately depicts a view in cross-section taken through patient 22 in the plane of x-ray fan beam 16.

The above-described prior art embodiment is useful for single-slice systems in which fan-beam backprojection is utilized for reproduction. Known embodiments of imaging system 10 that employ a multislice detector array 18 also employ only fan-bean backprojection for reconstruction. However, to produce better quality images, it would be desirable to efficiently take into account the additional dimension across detector rows. It would also be desirable to render three-dimensional images with greater precision than is possible when using fan-beam backprojection for reconstruction.

BRIEF SUMMARY OF THE INVENTION

There is therefore provided, in one embodiment of the present invention, a method for reconstructing a volume image of an object. The method includes steps of scanning an object with a multislice computed tomographic (CT) imaging system having a multislice detector array to acquire projection data of a volume of the object; filtering the acquired projection data; and backprojecting the filtered projection data to reconstruct voxels of the volume image. The multislice detector array has a plurality of rows and columns of detector elements and the backprojecting includes interpolating the filtered projection data across both rows and columns of the multislice detector array.

Embodiments of the present invention, such as the embodiment described above, produce improved image quality by efficiently taking into account the additional dimension across detector rows. Three-dimensional images are rendered with greater precision than is possible when using fan-beam backprojection for reconstruction.

BRIEF DESCRIPTION OF THE DRAWINGS

FIG. 3 is a prior art drawing illustrating the planar fan beam geometry of an imaging system having single-slice detector array.

FIG. 4 is a prior art backprojection system for a CT imaging system such as the one shown in FIG. 1.

DETAILED DESCRIPTION OF THE INVENTION

Figure 1:
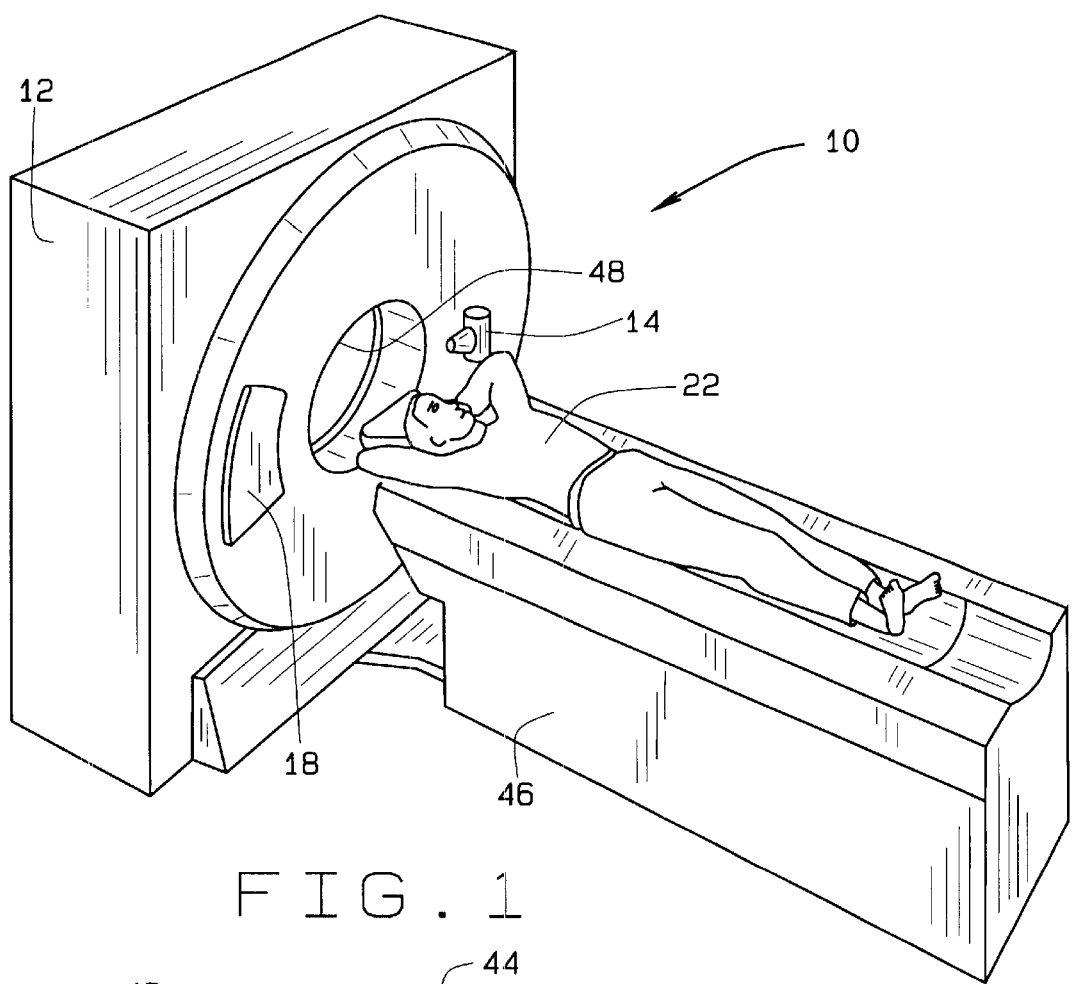
FIG. 1 is a pictorial view of a CT imaging system.
Figure 2:
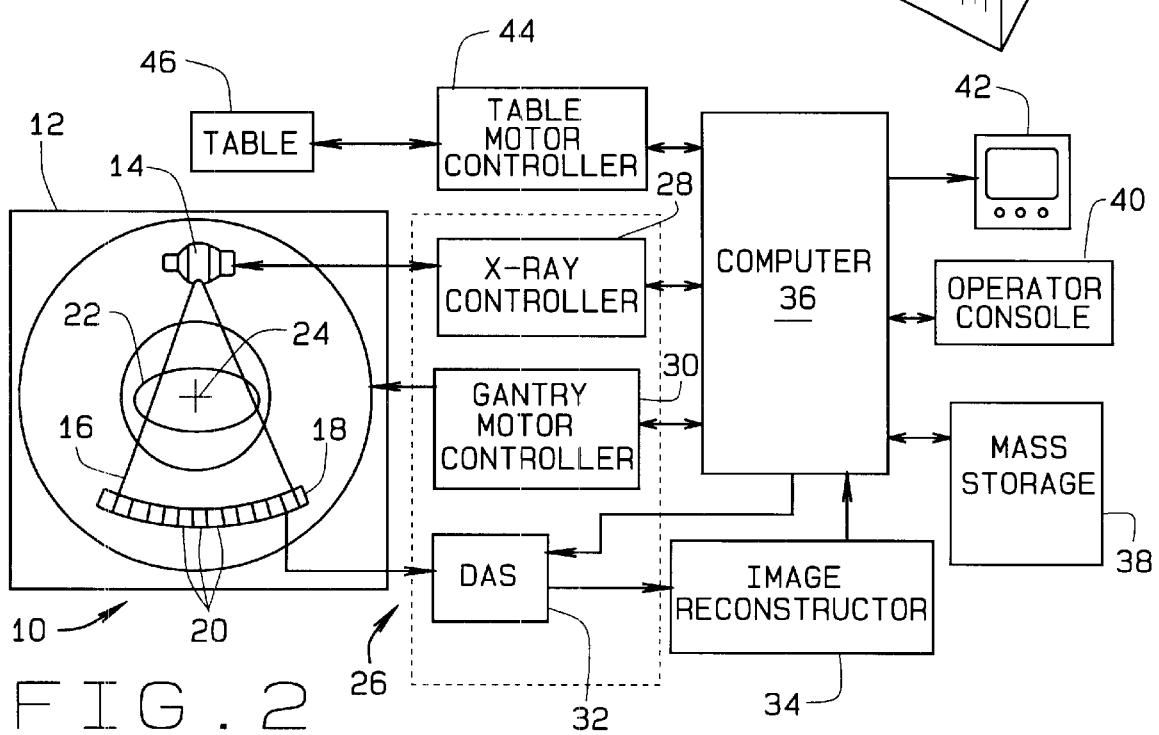
FIG. 2 is a block schematic diagram of the system illustrated in FIG. 1.
Figure 5:
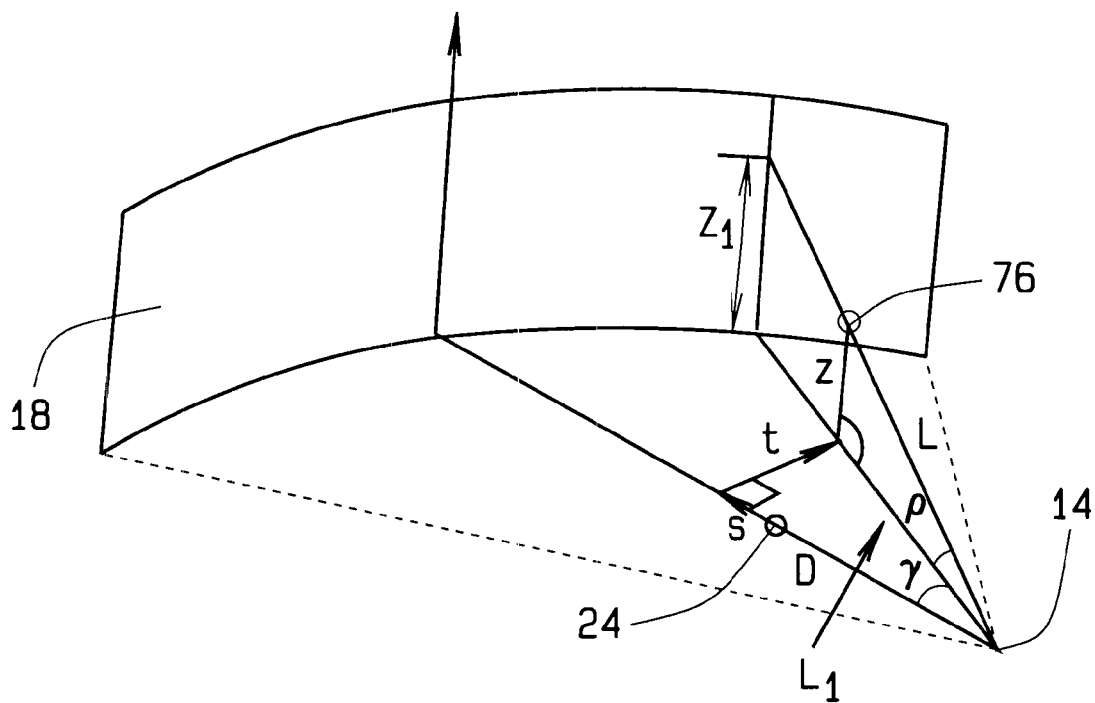
FIG. 5 is a drawing illustrating the three-dimensional geometry of an imaging system having a multislice detector array.
Figure 6:
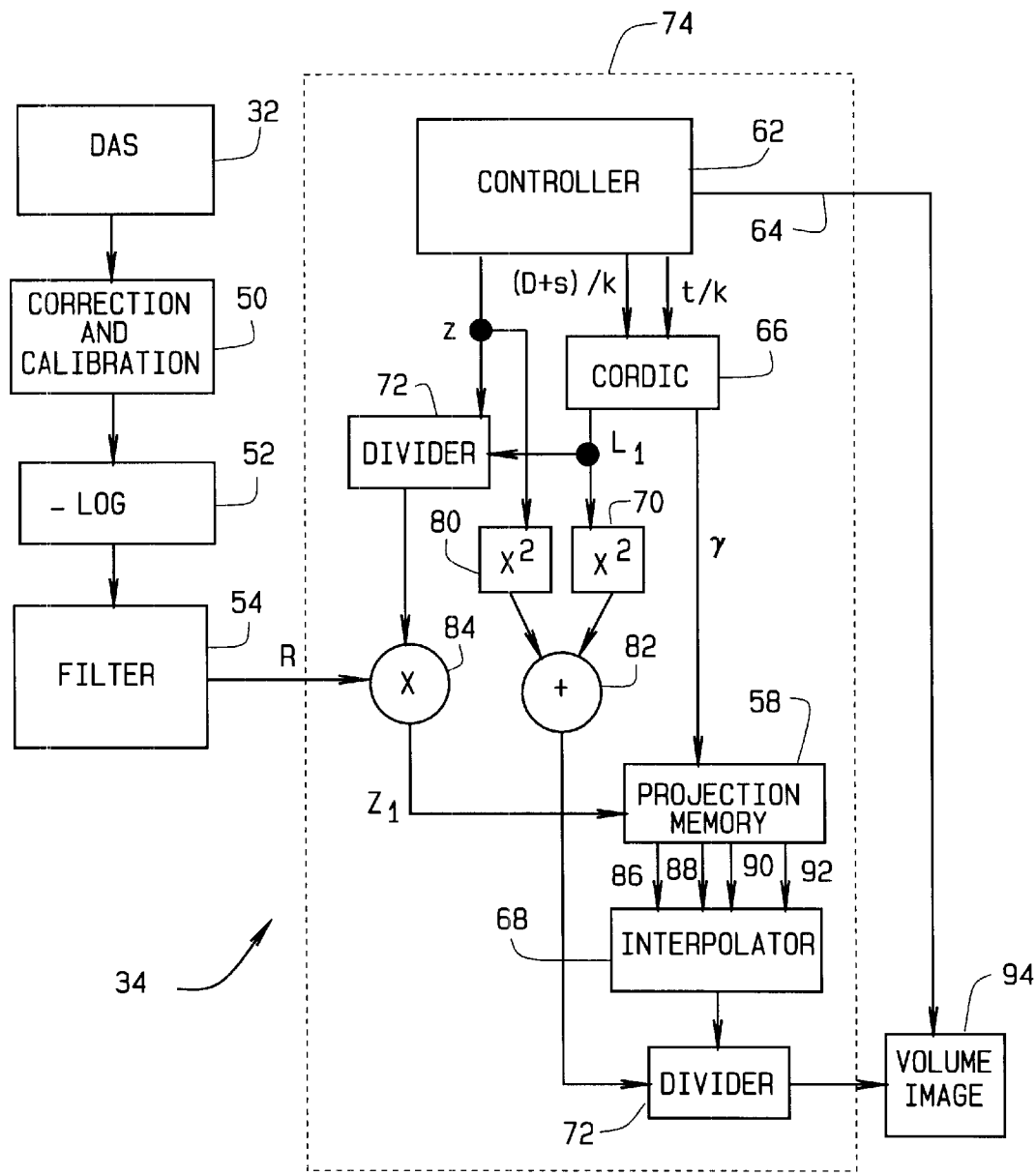
FIG. 6 is a simplified block diagram of a first embodiment of a special purpose cone beam backprojector of the present invention.

In one embodiment and referring to FIGS. 3, 5 and 6, a hardware backprojector 74 provides cone-beam backprojection for a multislice CT imaging system 10, thus providing an improvement over two-dimensional fan-beam reconstruction. Hardware backprojector 74 utilizes a CORDIC processor 66 that receives a voxel 76 (i.e., a three-dimensional picture element) location as an input. (It will be understood that the parameters used to describe the projection of voxel 76 onto the x-y plane of FIG. 3 also apply to voxel 76. The addition of a third dimension, i.e., a z-direction, also introduces new parameters, as shown in FIG. 5.)

A voxel 76 location is input to CORDIC processor 66 as the quantities (D+s)/k and t/k. The quantity 1/k is a constant scaling factor that is based on the number of pipeline stages used to implement CORDIC processor 66, as is known in the art. CORDIC processor 66 produces the quantities $L_1$ and $\gamma$. Divider 72 computes $z/L_1$, where z is the distance of voxel 70 from the x-y plane, i.e., a plane that includes isocenter 24. In addition, squarer 80 computes $z^2$, squarer 70 computes $(L_1)^2$, and adder 82 computes the quantity $[Z^2+(L_1)^2]$. Multiplier 84 computes $$z_1 = r\left(\frac{z}{L_1}\right),$$

where r is the distance from x-ray source to the detectors.

It is rare for a voxel 76 location to project precisely onto a detector cell 20. More generally, each voxel 76 projects against a point part of the way between two rows and two columns of detector elements 20 in detector array 18. Thus, the values $z_1$ and $\gamma$ for voxel 76 are used to read the four adjacent values from projection memory 58 that are nearest the projected voxel 76 location. These four values, in conjunction with the values $z_1$ and $\gamma$, are applied to interpolator 68 which linearly interpolates between the four values to produce the filtered projection value R. Thus, each voxel 76 is computed as a weighted interpolation of four measurements 86, 88, 90, and 92 from projection memory 58 by interpolator 68. The resulting interpolated pixel value R from interpolator 68 is divided by $L^2$ from adder 82. Divider 72 handles this division, and volume image 94 is updated using the result.

To summarize, for each voxel 76 in the reconstructed image, the channel angle $\gamma$ of the multislice projection data and the distance $L_1$ of the pixel from the x-ray source in the X-Y plane is calculated by CORDIC processor 66 which receives as inputs voxel 76 locations. The distance $L_1$ calculated by CORDIC processor 66 as well as the distance in Z from voxel 76 to a plane of reconstruction is used to calculate the distance L of voxel 76 from x-ray source 14 in the x-y-z volume and the distance (and therefore the slice location) of voxel 76 projected onto the detector plane. The formulas used to calculate these quantities are written as follows:

$$z_1 = R\left(\frac{z}{L_1}\right), \text{ and}$$

$$L^2 = (L_1)^2 + z^2.$$

The quantity $L^2$ is used for the scaling factor in the backprojection process.

Figure 7:
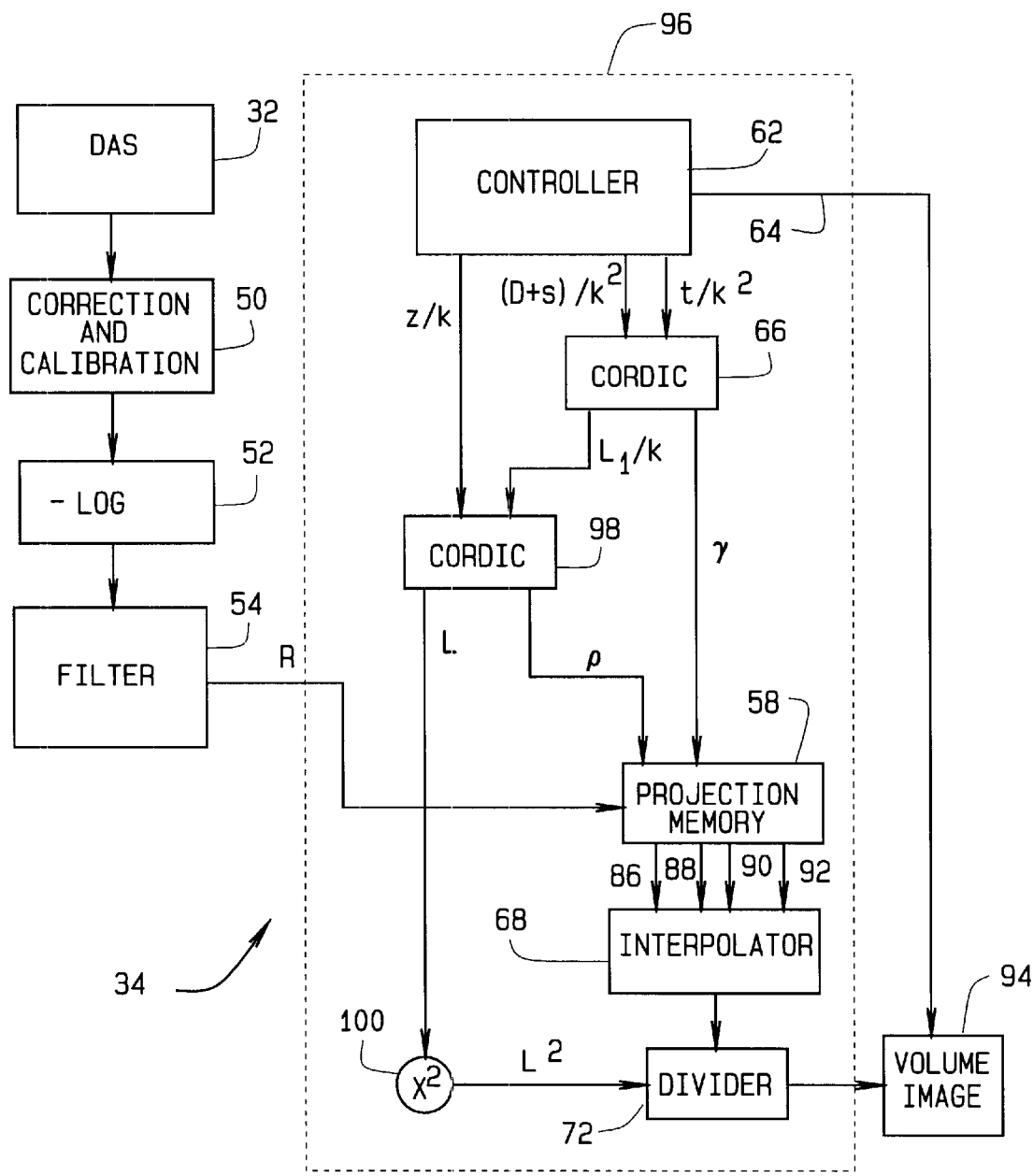
FIG. 7 is a simplified block diagram of a second embodiment of a special purpose cone beam backprojector of the present invention.

In another embodiment 96 of the present invention and referring to FIG. 7, two CORDIC processors 66 and 98 are used. CORDIC processor 98 functions in a manner similar to that of CORDIC processor 66 of backprojector embodiment 74 of FIG. 6. However, in embodiment 96, detector samples are given as $R(\beta,\gamma,\rho)$ and inputs to CORDIC processors 66 and 98 are scaled by $1/k^2$ rather than by $1/k$. This scaling has no effect on output $\gamma$ of CORDIC processor 66, but the other output is $L_1/k$ rather $L_1$, so that the $L_1/k$ output is already scaled for use as an input to CORDIC processor 98. CORDIC processor 98 accepts this input and another input z/k, and produces as output the quantities L and $\mu$, which correspond to a location of a voxel such as voxel 76. The value L is squared by squarer 100. Projection memory 58, interpolator 68, divider 72, and volume image 94 are counterparts to similar components in embodiment 74.

More particularly, projection memory 58 stores discrete projection data $R(\beta,\gamma,\rho)$ where $\rho$ is a cone angle. (Cone angle $\rho$ is related to a row number of detector array 18.) Angles $(\gamma,\rho)$ that are calculated by CORDIC processor 98 do not necessarily coincide with a grid for which discrete projection data $R(\beta,\gamma,\rho)$ is available. Therefore, interpolator 68 performs bilinear interpolations of the available values to obtain values corresponding to angles $(\gamma,\rho)$ that are calculated by CORDIC processor 98. Two values are required for each angle $\gamma$ and $\rho$. The computation is performed using integers and fractions, respectively. After dividing a CT number contributed by a particular radiation beam to voxel 76, the value is added to an accumulator. A summation of data over each radiation beam passing through each voxel 76 produces the final CT number.

It will readily be observed that embodiments of the present invention provide improved backprojection of attenuation data acquired during a scan to form an image. More specifically, by employing cone-beam backprojection rather than fan-beam backprojection, improved volume imaging is achieved because the additional dimension across detector rows is taken into account. In addition, interpolation of detector data is performed in two dimensions rather than just one, which results in a further imaging improvement.

While the invention has been described in terms of various specific embodiments, those skilled in the art will recognize that the invention can be practiced with modification within the spirit and scope of the claims.

What is claimed is:

1. A method for reconstructing a volume image of an object, said method comprising:
    scanning an object with a multislice computed tomographic (CT) imaging system having a multislice detector array to acquire projection data of a volume of the object;
    filtering the acquired projection data;
    backprojecting the filtered projection data to reconstruct voxels of the volume image;
    wherein the multislice detector array has a plurality of rows and columns of detector elements and said backprojecting including interpolating the filtered projection data across both rows and columns of the multislice detector array; and
    providing a CORDIC processor with inputs indicative of the voxel location, said inputs including:
        a first input (t/k) indicative of a distance of said voxel location from an isocenter as measured in a direction perpendicular to a ray of radiation in a view passing through the isocenter; and
        a second input ((D+s)/k) indicative of the distance of the isocenter from the radiation source plus the distance of the voxel location from the isocenter as measured in the direction of a ray of radiation in the view passing through the isocenter.

2. A method in accordance with claim 1 and further comprising, for each voxel of the volume image, the step of determining a channel angle $\gamma$ and a distance $L_1$ of the voxel from a radiation source of the CT imaging system in an x-y plane using a first CORDIC processor that receives as inputs a location of the voxel.

3. A method in accordance with claim 2 and further comprising, for each voxel, the step of determining a distance L of the voxel from the radiation source and a distance of the voxel projected on the detector array using the determined distance $L_1$ and a distance in a z-direction from the radiation source to a plane of reconstruction.

4. A method in accordance with claim 3 wherein the step of backprojecting the filtered projection data comprises the step of utilizing the quantity $L^2$ as a scaling factor.

5. A method for reconstructing a volume image of an object, said method comprising:

scanning an object with a multislice computed tomographic (CT) imaging system having a multislice detector array to acquire projection data of a volume of the object;

filtering the acquired projection data;

backprojecting the filtered projection data to reconstruct voxels of the volume image;

wherein the multislice detector array has a plurality of rows and columns of detector elements and said backprojecting including interpolating the filtered projection data across both rows and columns of the multislice detector array;

for each voxel of the image volume, determining a channel angle γ and a distance $L_1$ of the voxel from a radiation source of the CT imaging system in an x-y plane using a first CORDIC processor that receives as inputs a location of the voxel; and for each voxel of the volume image, determining a row angle ρ to be applied to the voxel and a distance L to the voxel from the radiation source utilizing a second CORDIC processor.

6. A method in accordance with claim 5 wherein said step of determining a row angle ρ and a distance L comprises the step of providing, to the second CORDIC processor, the value $L_1$ determined from the first CORDIC processor and a value indicative of a distance z from the voxel to the plane of reconstruction.

7. A method in accordance with claim 6 further comprising the step of providing the first CORDIC processor with inputs indicative of the voxel location, said inputs including:

a first input $(t/k^2)$ indicative of a distance of said voxel location from an isocenter as measured in a direction perpendicular to a ray of radiation in a view passing through the isocenter; and a second input $((D+s)/k^2)$ indicative of the distance of the isocenter from the radiation source plus the distance of the voxel location from the isocenter as measured in a direction of a ray of radiation in a view passing through the isocenter.

8. A method in accordance with claim 7 wherein the value indicative of a distance z from the voxel to the plane of reconstruction is (z/k).

9. A computed tomographic (CT) imaging system having a rotating gantry and a radiation source and a multislice detector array opposite one another on the rotating gantry, said CT imaging system configured to:

scan an object to acquire projection data of a volume of the object;

filter the acquired projection data; and backproject the filtered projection data to reconstruct voxels of a volume image of the object;

wherein said multislice detector array has a plurality of rows and columns of detector elements, and to backproject the filtered projection data, said CT imaging system is configured to interpolate the filtered projection data across both rows and columns of said multislice detector array; and provide a CORDIC processor with inputs indicative of the voxel location, said inputs including:

a first input (t/k) indicative of a distance of said voxel location from an isocenter as measured in a direction perpendicular to a ray of radiation in a view passing through the isocenter; and a second input ((D+s)/k) indicative of the distance of the isocenter from the radiation source plus the distance of the voxel location from the isocenter as measured in the direction of a ray of radiation in the view passing through the isocenter.

10. A CT imaging system in accordance with claim 9 further comprising a first CORDIC processor and further configured to determine, for each voxel of the volume image, a channel angle γ and a distance $L_1$ of the voxel from said radiation source in an x-y plane using said first CORDIC processor, said first CORDIC processor configured to input a location of the voxel.

11. A CT imaging system in accordance with claim 10 and further configured to determine, for each voxel, a distance L of the voxel from said radiation source and a distance of the voxel projected on said detector array using the determined distance $L_1$ and a distance in a z-direction from said radiation source to a plane of reconstruction.

12. A CT imaging system in accordance with claim 11 configured to utilize the quantity $L^2$ as a scaling factor to backproject the filtered projection data.

13. A computed tomographic (CT) imaging system having a rotating gantry, a radiation source, a multislice detector array opposite one another on the rotating gantry, a first CORDIC processor, and a second CORDIC processor, said CT imaging system configured to:

scan an object to acquire projection data of a volume of the object;

filter the acquired projection data; and backproject the filtered projection data to reconstruct voxels of a volume image of the object;

wherein said multislice detector array has a plurality of rows and columns of detector elements, and to backproject the filtered projection data, said CT imaging system is configured to interpolate the filtered projection data across both rows and columns of said multislice detector array;

determine, for each voxel of the volume image, a channel angle γ and a distance $L_1$ of the voxel from said radiation source in an x-y plane using said first CORDIC processor, said first CORDIC processor configured to input a location of the voxel; and determine, for each voxel of the volume image a row angle ρ to be applied to the voxel and a distance L to the voxel from said radiation source utilizing said second CORDIC processor.

14. A CT imaging system in accordance with claim 13 wherein to determine a row angle ρ and a distance L, said CT imaging system is configured to provide, as inputs to the second CORDIC processor, the value $L_1$ determined from said first CORDIC processor and a value indicative of a distance z from the voxel to the plane of reconstruction.

15. A CT imaging system in accordance with claim 14 further configured to provide said first CORDIC processor with inputs indicative of the voxel location, said inputs including:

a first input $(t/k^2)$ indicative of a distance of said voxel location from an isocenter as measured in a direction perpendicular to a ray of radiation in a view passing through the isocenter; and a second input $((D+s)/k^2)$ indicative of the distance of the isocenter from said radiation source plus the distance of the voxel location from the isocenter as measured in a direction of a ray of radiation in a view passing through the isocenter.

16. A CT imaging system in accordance with claim 15 wherein said value indicative of a distance z from the voxel to the plane of reconstruction is $(z/k)$.

* * * * *